(12) United States Patent
Short et al.

(10) Patent No.: US 8,409,874 B2
(45) Date of Patent: Apr. 2, 2013

(54) REVERSIBLE BINDING SURFACE

(75) Inventors: Rob Short, Sheffield (GB); Anthony J. Day, Oxford (GB)

(73) Assignee: Corning Incorporated, Corning, NY (US)

( * ) Notice: Subject to any disclaimer, the term of this patent is extended or adjusted under 35 U.S.C. 154(b) by 1191 days.

(21) Appl. No.: 10/599,943

(22) PCT Filed: Apr. 7, 2005

(86) PCT No.: PCT/GB2005/001369
§ 371 (c)(1),
(2), (4) Date: Jun. 29, 2007

(87) PCT Pub. No.: WO2005/099894
PCT Pub. Date: Oct. 27, 2005

(65) Prior Publication Data
US 2008/0003659 A1    Jan. 3, 2008

(30) Foreign Application Priority Data

Apr. 15, 2004 (GB) .................................. 0408351.5

(51) Int. Cl.
*C07H 1/06* (2006.01)
*B01J 20/32* (2006.01)
*B01J 20/34* (2006.01)

(52) U.S. Cl. .............. 436/501; 435/4; 435/7.1; 436/518

(58) Field of Classification Search .................. None
See application file for complete search history.

(56) References Cited

U.S. PATENT DOCUMENTS

| 5,455,040 | A | 10/1995 | Marchant |
| 6,042,875 | A | 3/2000 | Ding et al. |
| 2003/0113478 | A1 | 6/2003 | Dang et al. |

FOREIGN PATENT DOCUMENTS

| WO | WO 94/10938 | * | 5/1994 |
| WO | WO 98/19161 | * | 5/1998 |
| WO | WO 98/59360 | * | 12/1998 |
| WO | WO 01/31339 | | 5/2001 |
| WO | WO 03/030958 | | 4/2003 |
| WO | WO 2004/040308 | * | 5/2004 |

OTHER PUBLICATIONS

Schwarz et al. Glycobiology, 2003, vol. 13, No. 11, p. 749-754.*
Sigma Catalog, 2000-2001, p. 337.*
Dako General ELISA Procedure, Feb. 2002.*
Yuan et al. "Immobilization of high-affinity heparin oligosaccharides to radiofrequency plasma-modified polyethylene," J. Biomed. Materials Res., 1993, vol. 27, pp. 811-819.*
Mahoney et al., "A method for the non-covalent immobilization of heparin to surfaces," Anal. Biochem., 2004, vol. 330, pp. 123-129; Available on line May 8, 2004.*
Parkar et al., "Overlapping sites on the Link module of human TSG-6 mediate binding to hyaluronan and chondroitin-4-sulfate," FEBS Lett., 1997, vol. 410, pp. 413-417.*

* cited by examiner

*Primary Examiner* — Shafiqul Haq
*Assistant Examiner* — Galina Yakovleva
(74) *Attorney, Agent, or Firm* — Hoffmann & Baron, LLP

(57) ABSTRACT

The present invention relates to a method to treat a product which product comprises a surface which surface includes a plasma polymer of an organic monomer wherein immobilized on said plasma polymerized surface is at least one biological entity comprising, contacting said product with an agent that promotes, either directly or indirectly, the disassociation of said entity from said product.

Figure 1:
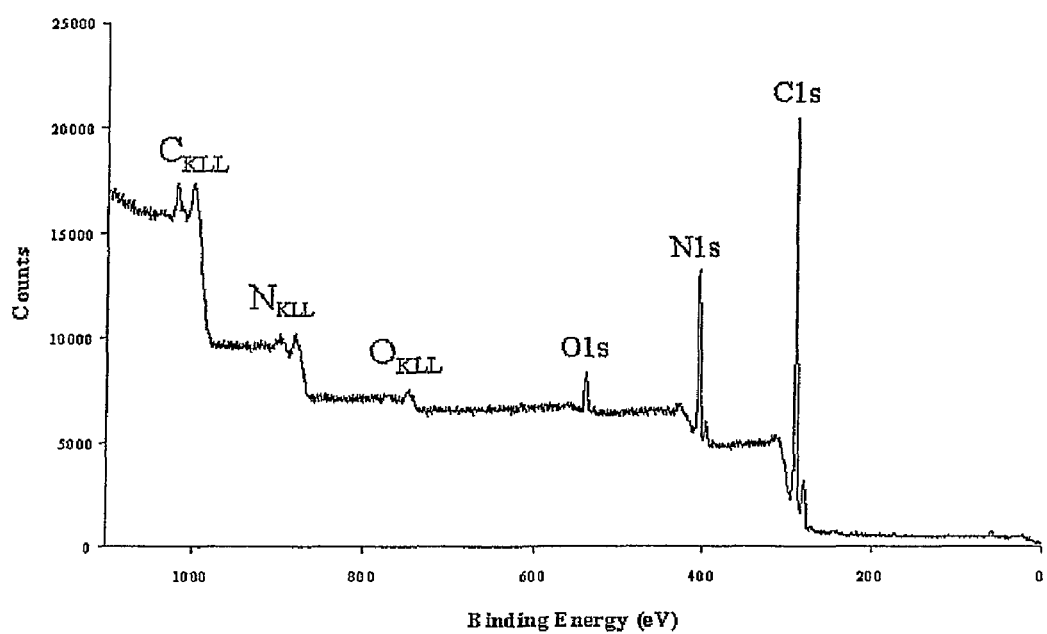

6 Claims, 6 Drawing Sheets a b

REVERSIBLE BINDING SURFACE

CROSS REFERENCE TO RELATED APPLICATIONS

This is a national stage filing in accordance with 35 U.S.C. § 371 of PCT/GB2005/001369, filed Apr. 7, 2005, which claims the benefit of the priority of United Kingdom Patent Application No. GB 0408351.5, filed Apr. 15, 2004.

The invention relates to a method for the separation and/or purification of biological molecules and/or complexes of biological molecules, for example cells or viruses.

Affinity purification of biological molecules, for example proteins, is known in the art and allows the purification of molecules by exploiting the binding affinity of the target molecule for a molecular binding partner. For example, *Staphylococcus* Protein A will bind immunoglobulin G and this has been used to purify and/or concentrate antibodies from serum. Further examples of "affinity tags" include, maltose binding protein, glutathione S transferase, calmodulin binding protein and the engineering of polyhistidine tags into proteins that are then purified by affinity purification on nickel containing matrices. These systems exploit the binding affinity of one protein for another protein. Proteins also bind nucleic acid and carbohydrates and the affinity of proteins for these molecules has also been exploited to isolate and/or purify and/or separate proteins.

WO01/31339 describes the use of a technique called plasma polymerisation. The technique is used to fabricate the surfaces of products, for example assay products, to provide surfaces with unique chemical properties that bind biological molecules, for example proteins and nucleic acid and the detection of these molecules bound to the plasma polymerised surface.

Plasma polymerisation is a technique that allows an ultrathin (e.g. ca.200 nm) cross linked polymeric film to be deposited on substrates of complex geometry and with controllable chemical functionality. As a consequence, the surface chemistry of materials can be modified, without affecting the bulk properties of the substrate so treated. Plasmas or ionised gases are commonly excited by means of an electric field. They are highly reactive chemical environments comprising ions, electrons, neutrals (radicals, metastables, ground and excited state species) and electromagnetic radiation. At reduced pressure, a regime may be achieved where the temperature of the electrons differs substantially from that of the ions and neutrals. Such plasmas are referred to as "cold" or "non-equilibrium" plasmas. In such an environment many volatile organic compounds (e.g. volatile alcohol containing compounds, volatile acid containing compounds, volatile amine containing compounds, or volatile hydrocarbons, neat or with other gases, e.g. Ar) have been shown to polymerise (H.K. Yasuda, Plasma Polymerisation, Academic Press, London 1985) coating both surfaces in contact with the plasma and those downstream of the discharge. The organic compound is often referred to as the "monomer". The deposit is often referred to as "plasma polymer". The advantages of such a mode of polymerisation potentially include: ultra-thin pin-hole free film deposition; plasma polymers can be deposited onto a wide range of substrates; the process is solvent free and the plasma polymer is free of contamination.

Under conditions of low power, plasma polymer films can be prepared which retain a substantial degree of the chemistry of the original monomer. For example, plasma polymerised films of acrylic acid contain the carboxyl group (O'Toole L., Beck A. J., Short R. D., Macromolecules, 1996, 29, 5172-5177). The low power regime may be achieved either by lowering the continuous wave power, or by pulsing the power on and off (Fraser S., Barton D., Bradley J. W., Short R. D., J. Phys. Chem. B., 2002, 22(106), 5596-5608). Co-polymerisation of one or more compounds having functional groups with a hydrocarbon allows a degree of control over surface functional group concentrations in the resultant plasma copolymer (PCP) (Beck, A. J, Jones F. R., Short R. D., Polymer 1996, 37(24) 5537-5539). Suitably, the monomers are ethylenically unsaturated. Thus the functional group compound maybe unsaturated carboxylic acid, alcohol or amine, for example, whilst the hydrocarbon is suitably an alkene. By plasma polymerisation, it is also possible to deposit ethylene oxide-type molecules (eg. tetraethyleneglycol monoallyl ether) to form 'non-fouling' surfaces. It is also possible to deposit perfluoro-compounds (i.e. perfluorohexane, hexafluoropropylene oxide) to form hydrophobic/superhydrophobic surfaces. This technique is advantageous because the surfaces have unique chemical and physical characteristics. Moreover, the surface wettability, adhesion and frictional/wear characteristics of the substrate can be modified in a controllable and predictable manner.

In our co-pending application, PCT/GB03/004653 (currently unpublished), we disclose a method to fabricate surfaces with plasma polymers formed from organic monomers that provide surfaces with chemical finctionalities that bind carbohydrates.

Polymers of sugars are referred to as polysaccharides. Polysaccharides that are composed of the same sugars they are referred to as a homopolysaccharides. If they are of different sugars they are referred to as heteropolysaccharides. The most abundant heteropolysaccharides in the body are the glycosaminoglycans (GAGs) also referred to as anionic mucopolysaccharides. These molecules are long unbranched polysaccharides containing a repeating disaccharide unit. The disaccharide units contain either of two modified sugars galactosamine (Gal) or glucosamine (Glc) and an uronic acid such as glucuronate or iduronate. GAGs are highly negatively charged molecules, with extended conformation that imparts high viscosity to a solution containing the GAGs. GAGs are located primarily on the surface of cells or in the extracellular matrix. The GAGs of physiological significance are hyaluronan, dermatan sulfate, chondroitin sulfate, heparin, heparan sulphate, and keratan sulphate.

PCT/GB03/004653 describes methodology that allows polysaccharides to passively bind surfaces comprising plasma polymers to form a stable interface to which the polysaccharides may bind in a native conformation. The bound polysaccharides may then interact with biological molecules, for example proteins, to effect immobilisation and/or isolation of the molecules from, for example, a complex mixture.

We describe herein a methodology that allows the selective removal of molecules (e.g. protein, nucleic acid, carbohydrate) bound to a plasma polymerised surface.

This can also be used for the removal of molecules subsequently bound to protein, nucleic acid or carbohydrate from a plasma polymerised surface.

The surface, after treatment, remains functionally intact and re-usable. The method is versatile since it allows the removal of a surface coat from a plasma polymerised surface and the application of a second, different surface coat to the plasma polymerised surface. The methodology can be modified to allow for the selective removal of other biomolecules (e.g. nucleic acids and proteins or cells/virus particles) from a plasma polymerised surface.

According to an aspect of the invention there is provided a method to treat a product which product comprises a surface which surface includes a plasma polymer of an organic monomer wherein immobilised on said surface is at least one biological entity comprising, contacting said product with an agent that promotes, either directly or indirectly, the disassociation of said entity from said product.

In a preferred method of the invention said biological entity is a polypeptide.

In an alternative preferred method of the invention said biological entity is a carbohydrate.

In a still further alternative preferred method of the invention said biological entity is a nucleic acid molecule. Preferably said nucleic acid molecule is selected from the group consisting of: DNA (e.g. cDNA or genomic DNA or an oligonucleotide), RNA or peptide oligonucleotides (PNA's), single stranded DNA.

In a yet further preferred method of the invention said biological entity is a cell or viral particle.

"Product" may be defined as an assay product, for example a micro-titre plate, glass slide, array device or chip, microbead, fibre or fabric that may be woven or non-woven, membrane (e.g. nitrocellulose, nylon), microfluidic device, lab on a chip, or therapeutic vehicle—valves (e.g. heart valves); prosthesis; implant; matrix; stent; biodegradable matrix; polymeric film; wound dressings e.g. bandages; gauze; tape; or plaster casts, bandage. Product may also be cell/tissue culture bottles or flasks if it is desired to isolate or purify cells or viral particles. The product may be manufactured from materials such as porous or non-porous materials for example glass, metals, ceramic and plastics. Plastics materials typically include polyethylene terephthalate, high density polyethylene, low density polyethylene, polyvinyl chloride, polypropylene or polystyrene.

"Agent" is defined as any means that results in the disassociation of molecules bound to the product of the invention. The interaction of carbohydrate with the plasma polymerised surface is an ionic interaction and therefore it will be apparent that any means that results in disruption of ionic bonding will release at least the biological entity from the plasma polymer surface. Examples include, but are not limited to, alteration in the ionic strength, modulation of pH, the use of detergents and solvents. It will also be apparent that an "agent" may be an environmental agent, for example alteration of temperature. Combinations of agent may also be used in the method of the invention. Conditions may also be determined that allow the removal of just a biological molecule bound to a protein, nucleic acid or carbohydrate molecule.

"Entity" is defined as any biological molecule or complex of molecules that bind a plasma polymerised surface or to a protein, nucleic acid or carbohydrate that is bound to a plasma polymerised surface and includes, by example and not by way of limitation, polypeptides or peptides, nucleic acid, viruses, cells, e.g. bacterial cells, mammalian cells, or plant cells.

In a preferred method of the invention and said surface comprises a plasma polymer of a volatile acid.

In a further preferred method of the invention said surface comprises at least 5% acid.

In an alternative preferred method of the invention said surface comprises a plasma polymer of a volatile alcohol.

In a further alternative method of the invention said surface comprises a plasma polymer of a volatile amine.

In a still further preferred method of the invention said surface comprises a mixture of volatile acid and volatile hydrocarbon.

Polymerisable monomers that may be used in the practice of the invention preferably comprise unsaturated organic compounds such as, olefinic carboxylic acids and carboxylates, olefinic amines, olefic alcohols, olefinic nitrile compounds, oxygenated olefins, halogenated olefins and olefinic hydrocarbons. Such olefins include vinylic and allylic forms. The monomer need not be olefinic, however, to be polymerisable. Cyclic compounds such as cyclohexane, cyclopentane and cyclopropane are commonly polymerisable in gas plasmas by glow discharge methods. Derivatives of these cyclic compounds, such as 1,2-diaminocyclohexane for instance, are also commonly polymerisable in gas plasmas. Particularly preferred are polymerisable monomers containing hydroxyl, amino or carboxylic acid groups. Of these, particularly advantageous results have been obtained through use of acrylic acid or allyl amine. Mixtures of polymerisable monomers may be used. Additionally, polymerisable monomers may be blended with other gases not generally considered as polymerisable in themselves, examples being argon, nitrogen and hydrogen. The polymerisable monomers are preferably introduced into the vacuum chamber in the form of a vapour. Polymerisable monomers having vapour pressures less than $1.3 \times 10^{-2}$ mbar (1.3 Pa) are not generally suitable for use in the practice of this invention.

Polymerisable monomers having vapour pressures of at least $6.6 \times 10^2$ mbar (6.6 Pa) at ambient room temperature are preferred. Where monomer grafting to plasma polymerisate deposits is employed, polymerisable monomers having vapour pressures of at least 1.3 mbar (130 Pa) at ambient conditions are particularly preferred.

To maintain desired pressure levels, especially since monomer is being consumed in the plasma polymerisations operation, continuous inflow of monomer vapour to the plasma zone is normally practiced. When non polymerisable gases are blended with the monomer vapour, continuous removal of excess gases is accomplished by simultaneously pumping through the vacuum port to a vacuum source, indeed this is the case when employing polymerisable monomers. Since some non-polymerisable gases are often evolved from glow discharge gas plasmas, it is advantageous to control gas plasma pressure at least in part through simultaneous vacuum pumping during plasma polymerisate deposition on a substrate in the process of this invention.

Monomers suited for this invention include, fully saturated and unsaturated carboxylic acid compounds up to 20 carbon atoms. More typically 2-8 carbons. Ethylenically unsaturated compounds (especially $\alpha,\beta$ unsaturated carboxylic acids) including acrylic acid, methacrylic acid. Saturated including ethanoic acid and propanoic acid. Alternatively, compounds that can be plasma polymerised that readily hydrolyse to give carboxylic acid functionalities, e.g. organic anhydrides (e.g. maleic anhydride) acyl chlorides may be used.

The glow discharge through the gas or blend of gases in the vacuum chamber may be initiated by means of an audiofrequency, a microwave frequency or a radiofrequency field transmitted to or through a zone in the vacuum chamber. Particularly preferred is the use of a radiofrequency (RF) discharge, transmitted through a spatial zone in the vacuum chamber by an electrode connected to an RF signal generator. A rather broad range of RF signal frequencies starting as low as 50 kHz may be used in causing and maintaining a glow discharge through the monomer vapor. In commercial scale usage of RF plasma polymerisation, an assigned radiofrequency of 13.56 MHz may be more preferable to use to avoid potential radio interference problems as with examples given later. Typically, using the composite ratio of W/FM, as described by Yasuda (1985) the power loading should be $<10^9$ J/kg to achieve functional group retention in plasma polymers. (W=power (J/min); F=flow rate (mole/min); M=average molecular mass (kg/mol) [Although flow rate is given as sccm, this is in fact not strictly correct. Conversion from sccm to mol/min can be readily performed by dividing scccm by 22,400).

The glow discharge need not be continuous, but may be intermittent in nature during plasma polymerisate deposition. Or, a continuous glow discharge may be employed, but exposure of a substrate surface to the gas plasma may be intermittent during the overall polymerisate deposition process. Or, both a continuous glow discharge and a continuous exposure of a substrate surface to the resulting gas plasma for a desired overall deposition time may be employed. The plasma polymerisate that deposits onto the substrate generally will not have the same elemental composition as the incoming polymerisable monomer (or monomers). During the plasma polymerisation, some fragmentation and loss of specific elements or elemental groups naturally occurs. Thus, in the plasma polymerisation of acrylic acid, carboxyl content of the plasma polymerisate is typically lower than would correspond to pure polyacrylic acid. Similarly, in the plasma polymerisation of allylamine, nitrogen content of the plasma polymerisate is typically lower than would correspond to pure polyallylamine. Exposure time to either of these unreacted monomers in the absence of a gas plasma, as through intermittent exposure to a glow discharge, allows for grafting of the monomer to the plasma polymerisate, thereby increasing somewhat the level of the functional group (carboxylic acid or amine) in the final deposit. Time intervals between plasma exposure and grafting exposure can be varied from a fraction of a second to several minutes.

In a preferred method of the invention said surface comprises a polymer comprising a nitrogen content of at least 2%. Preferably said nitrogen content is 2-20%. Alternatively said nitrogen content is greater than 20%. The percentages refer to the percent of nitrogen atoms in the surface. For example 20% nitrogen means that 20 of every one hundred atoms, excluding hydrogen, in the plasma polymer is nitrogen.

In a preferred method of the invention said plasma is created by means of electrical power input (radio frequency 13.56 MHz), coupled by means of a copper coil or bands.

The reactor volume is in the range 2-10 L and the reactor is pumped by means of a double stage rotary pump to a base pressure approaching $10^{-4}$ mbar. In the case of replacing the rotary pump with a turbomolecular pump better base pressures can be achieved. The monomer pressure is in the range $10^{-1}$ mbar to $10^{-3}$ mbar and the monomer flow rate is 1-20 cm$^3$/min (sccm). The power would be typically 0.1-50 W continuous wave. Those skilled in the art may adjust these parameters to produce like plasmas by pulsing on the micro or milli second time scales.

Plasma polymerised surfaces may be uniform or non-uniform. In our co-pending application WO03/001242, which is incorporated by reference, we describe the formation of non-uniform plasma polymerised surfaces. Non-uniform refers to surfaces that have a heterogeneous chemical and/or physical structure. WO03/001242 describes the deposition of plasma polymers with different chemistries and molecular architecture in a spatially restricted pattern, optionally at varying concentration, and at a micrometer resolution. This allows the fabrication of products with highly defined chemical and physical surface properties which advantageously; facilitates the binding and/or separation of different biological molecules and different concentrations of biological molecules followed by their detection and analysis; locally modifies the surface characteristics such as wettability, friction and wear and adhesion; and fabricates structures which through a combination of chemistry and structure act as switches, valves or pumps (upon receipt of an appropriate stimulus). The non-uniform surfaces allow the formation of regions within a surface to which biological entities can bind. This is particularly advantageous if a biological entity is trace or is expensive, or where a small of amount of material is to be extracted (from a large quantity) for subsequent processing.

In a preferred method of the invention said carbohydrate is a homopolysaccharide.

In an alternative preferred method of the invention said carbohydrate is a heteropolysaccharide. Preferably said heteropolysaccharide is a glycosaminoglycan.

In a preferred method of the invention said carbohydrate is a sulphated biomolecule, preferably highly sulphated.

In a further preferred method of the invention said glycosaminoglycan is selected from the group consisting of: hyaluronan; dermatan sulfate; chondroitin sulphate; heparin; heparan sulphate; or keratan sulphate.

Carbohydrate molecules are passively adsorbed and immobilised. Adsorption involves the incubation of a surface with the carbohydrate in solution, such that the carbohydrate binds with the surface. The binding should be sufficiently strong that the carbohydrate is immobilised to the surface to the extent that it cannot be desorbed by washing, or by the typical processes carried out in biochemical or chemical assays. The immobilised carbohydrate should be bound in such a manner that it retains its native biological activity, as demonstrated by binding with target biological entities that it would normally bind with it in solution.

Passive adsorption to plasma polymer surfaces may be carried out from a solution containing carbohydrate, over a range of pH. Preferably the pH is from 3 to 11, for example pH 4 to 10, 5 to 9, 6 to 8 or 7.

Passive adsorption to plasma polymer surfaces may be carried out from a solution containing carbohydrate concentrations (1 ng/ml-10 ng/ml 10-100 ng/ml, 100-1000 ng/ml, or even microgram quantities per ml [1-10 µg/ml]). Adsorption is most likely, but not exclusively, to be carried out in the temperature range of 20-37.5° C.

Adsorption may be carried out from phosphate buffered saline or a solution of physiological ionic strength.

It is well known to those skilled in the art that the adsorption of specific polysaccharides, for example polysaccharides carrying a high net negative charge (e.g. sulphated GAGs e.g. heparin) to plastic surfaces is difficult to achieve. Plasticware that is available for biochemical and chemical assays (e.g. culture dishes, 96 well microtitre plates etc.) is typically manufactured from polystyrene (although it may be surface treated to improve binding properties). Surface treatments may include corona, plasma, acid or alkaline rinses, and flame. These treatments introduce a range of new surface functionalities into the plastic, mainly oxygen (alcohols, ethers, carbonyls and carboxyls, as well as peroxides). But, alone, these functionalities do not promote the passive adsorption of negatively charged molecules.

It is preferred that the carbohydrate is adsorbed pure. Moreover it is preferred that the carbohydrate is not contaminated (e.g. with albumin or salts), or that the immobilisation surface is modified (for example by the binding of a first biomolecule (for example, albumin) that will in turn bind the polysaccharide.

Nucleic acid and protein is also susceptible to the method of the invention. For example, nucleic acid could modified (i.e. purified/chemically or biologically modified) and then removed, directly or indirectly, from the plasma polymerised surface. Alternatively, the inimobilised nucleic acid could be used to bind a second molecule (e.g. a complementary nucleic acid or a protein or carbohydrate), and this complex is removed. Moreover, an immobilised protein may be subsequently removed or may be used to bind a further biomolecule (protein, sugar, nucleic acid) and this complex is then removed from the surface.

According to a further aspect of the invention there is provided a method to treat a product which product comprises a surface which surface includes a plasma polymer of an organic monomer wherein immobilised on said surface is at least one biological entity, comprising the steps of
  i) contacting said product with an agent that promotes, either directly or indirectly, the disassociation of said biological entity from said product surface; and
  ii) contacting said product with a second, different, biological entity to provide a product surface with a different immobilised biological entity.

In a preferred method of the invention said biological entity is a carbohydrate. Preferably said carbohydrate is a homopolysaccharide.

In an alternative preferred method of the invention said carbohydrate is a heteropolysaccharide. Preferably said heteropolysaccharide is a glycosaminoglycan.

In a further preferred method of the invention said glycosaminoglycan is selected from the group consisting of: hyaluronan; dermatan sulfate; chondroitin sulphate; heparin; heparan sulphate; or keratan sulphate.

In a further preferred method of the invention said biological entity is a polypeptide.

In an alternative preferred method of the invention said biological entity is a nucleic acid.

In a further alternative method of the invention said biological entity is a cell or viral particle.

It will be apparent that the second biological entity may be the same chemical nature as the first immobilised biological entity (e.g. a first carbohydrate molecule and a second, different carbohydrate molecule) or of a different chemical nature (e.g. a first carbohydrate molecule and a second molecule that is a protein or nucleic acid). Various combinations are readily apparent to the skilled artisan.

Figure 2:
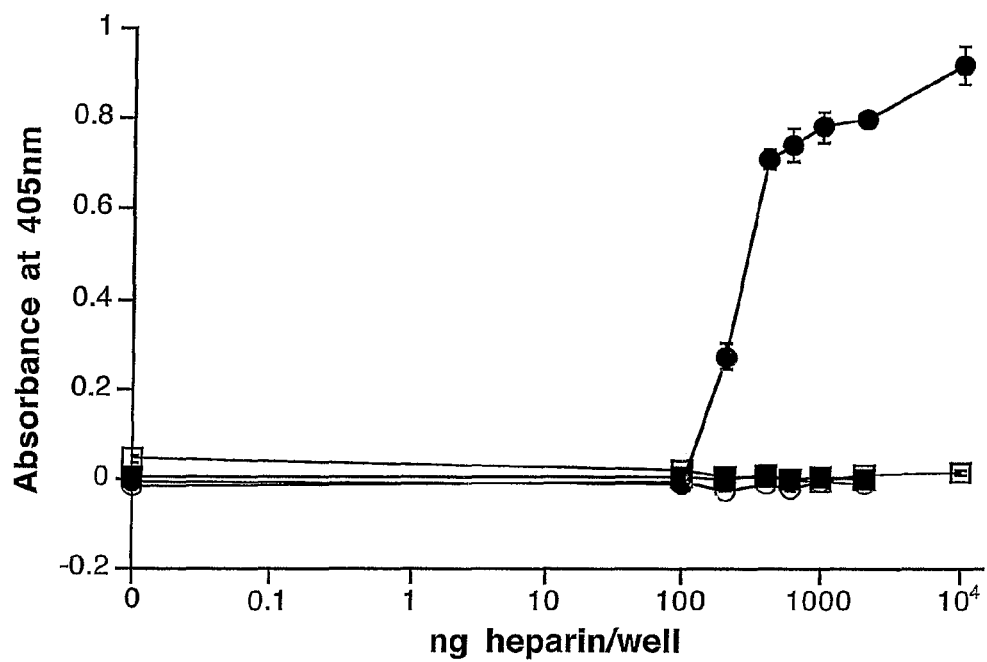
Figure 2:
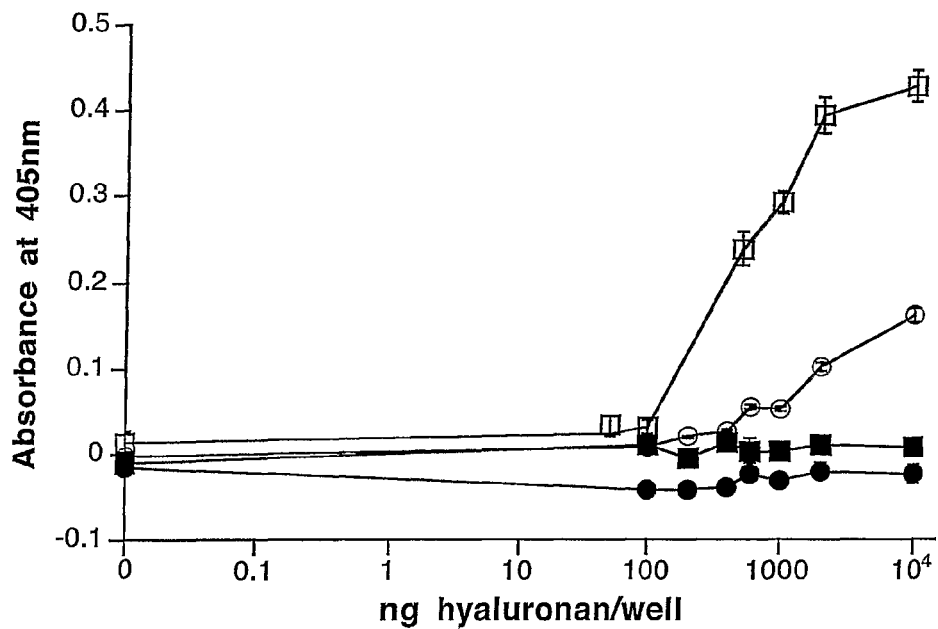
Figure 3:
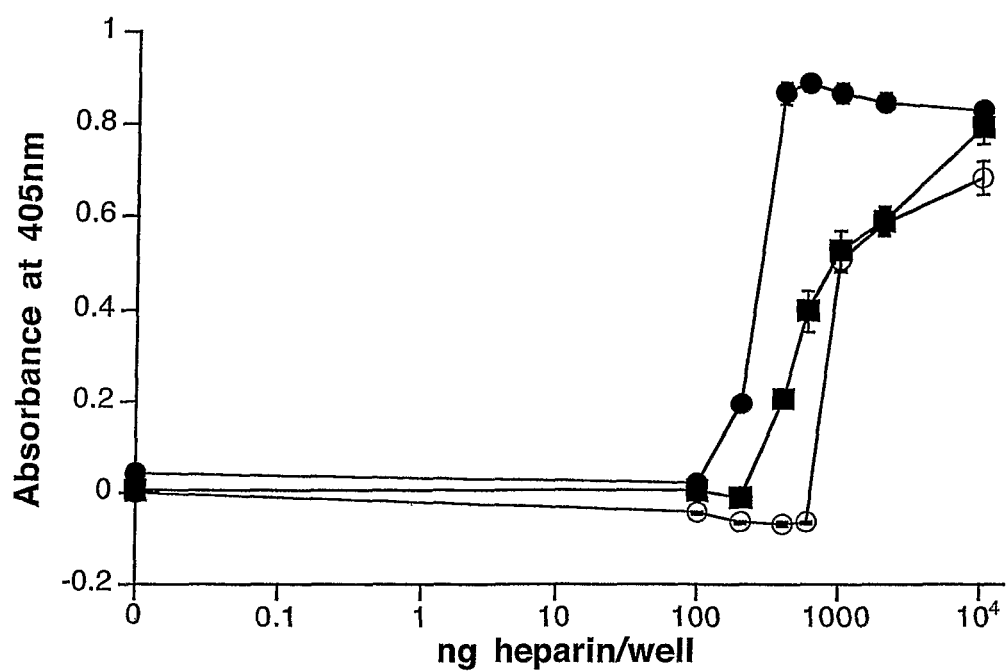
Figure 4:
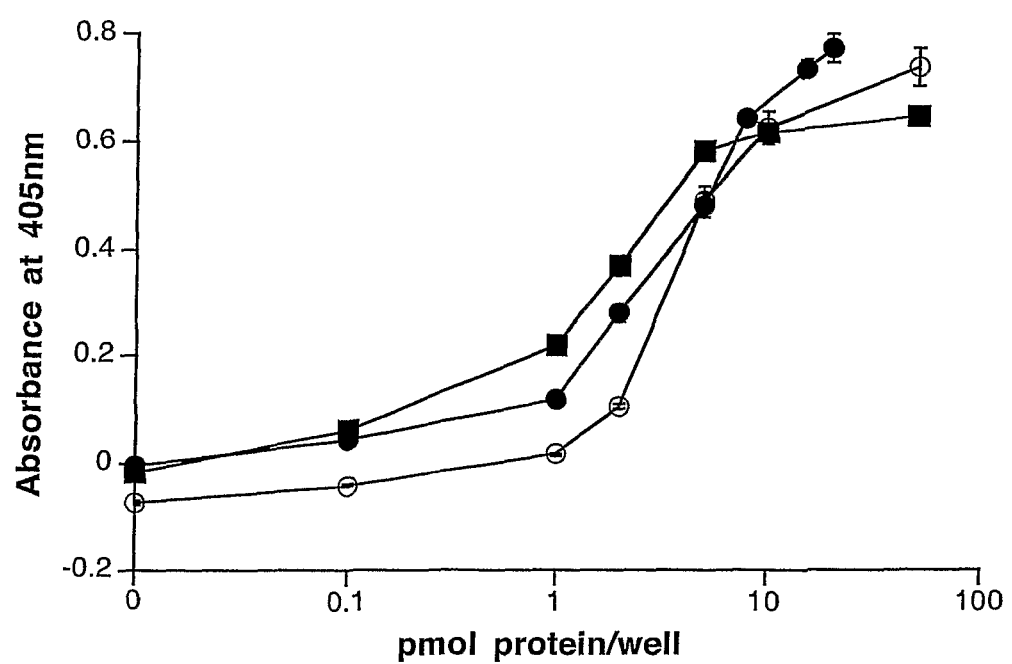

An embodiment of the invention will now be described by example only and with reference to the following figures:

FIG. 1. X-ray photoelectron spectroscopy (XPS) survey scan of allylamine plasma polymer (5W);

FIG. 2. The binding of bA-Link_TSG6 to untreated and allylamine-coated Nunc plates with a) high molecular weight Hp and b) umbilical cord HA. Values are plotted as mean absorbance at 405 nm after 40 min development time (n=4) ±S.E.M. Closed circle=PBS coated allylamine plate; closed square=Na2C03 coated allylamine plate; open circle=PBS coated standard plate; open square=Na2CO3 coated standard plate;

FIG. 3. The binding of bA-Link_TSG6 to allylamine plates coated with high molecular weight Hp (closed circle), low molecular weight Hp (closed square) and Hp dp10 (open circle). Values are plotted as mean percentage of absorbance at 405 nm after 40 min development time (n=4)±S.E.M;

FIG. 4. The interaction of Link_TSG6 (shown as closed circle), murine KC (open circle) and human IL-8 (closed square) with allylamine plates coated with high molecular weight Hp (1 µg, 0.5 µg and 0.5 µg/well, respectively). ELISAs were developed as described BELOW and data are plotted as mean percentage of absorbance at 405 nm (n=4) ±S.E.M.

Figure 5:
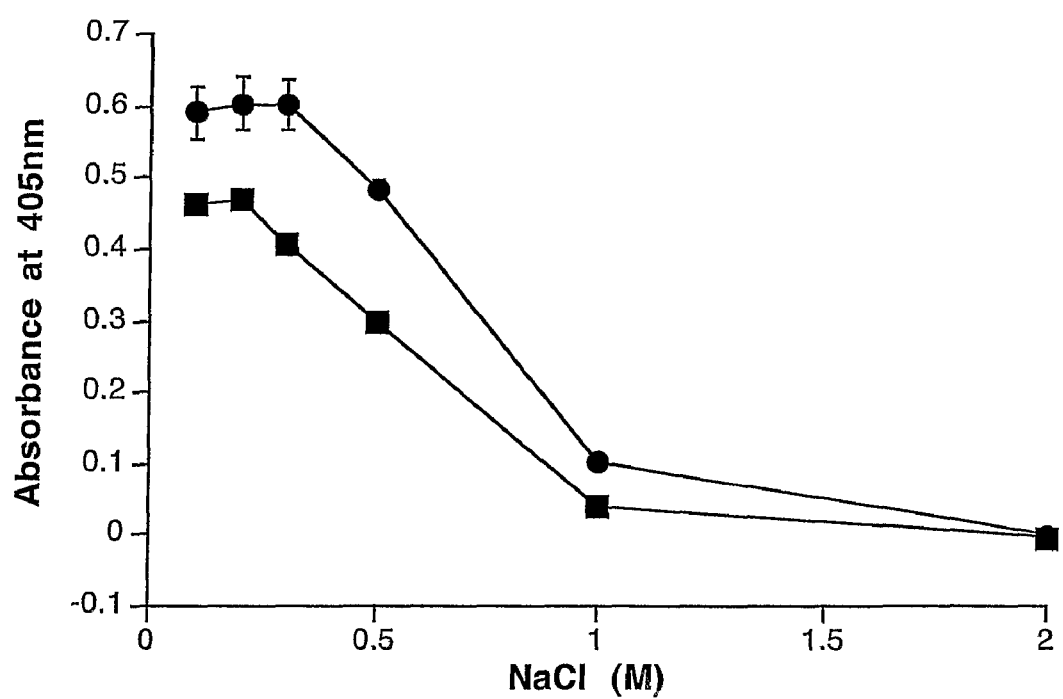
Figure 6:
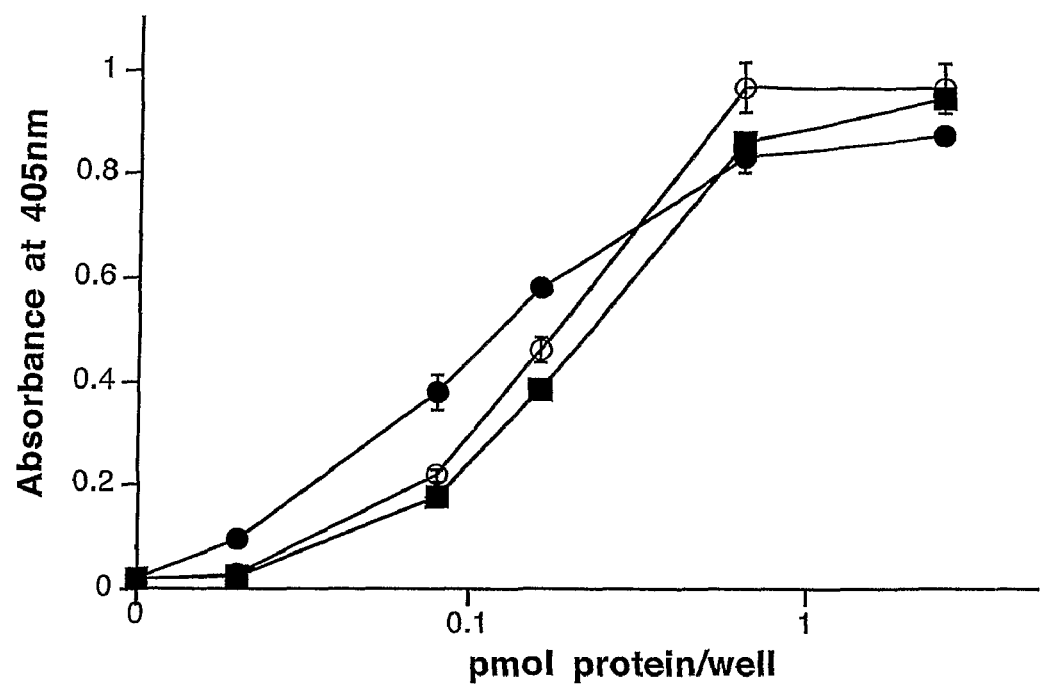

FIG. 5. Effect of salt-strength on the immobilization of heparin to allylamine plates. Allylamine plates were coated with 1 µg/well either high molecular weight Hp (closed circles) or a heparin dp10 oligomer (closed squares) and then incubated with varying concentrations of NaCl. Heparin remaining bound to the plates was detected using Link_TSG6 as described in the text. Data are shown as mean percentage of absorbance at 405 nm (n=4)±S.E.M; and FIG. 6. Effect of salt strength on the interaction of factor H with immobilized heparin. The interaction of factor H with immobilized high molecular weight heparin (1 µµg/well) was determined at 100 mM (closed circle), 250 mM (closed square) and 400 mM (open circle) NaCl. Data are shown as mean percentage of absorbance at 405 nm (n=4)±S.E.M.

MATERIALS AND METHODS

Reagents

The Link module from human TSG-6 (Link_TSG6) and mono-biotinylated Link_TSG6 (bA-Link_TSG6) were produced as described previously [28-30]. High molecular weight heparin was as reported in the 4th International Standard (NIBSC, UK; see [31, 32]). Low molecular weight heparin was purchased from Sigma, and a defined bovine lung heparin decasaccharide (dp10) was generated by heparinase I digestion as previously described [21]. Factor H was purified from human serum as described in [33] and detected using the OX23 monoclonal antibody [34]. Recombinant murine KC, human IL-8 and biotinylated anti-KC and anti-IL-8 polyclonal antibodies were purchased from PreproTech EC Ltd. (London, UK). Q75.2.10 (anti-TSG6Q mAb) was generated as described previously [35]. Microtitre plates were purchased from either Nunc Laboratories UK (MaxiSorp) or Bibby Sterilin. Development reagents for the assays, human umbilical cord hyaluronan (HA) and all other chemicals were as noted previously [30, 36, 37].

Plasma Polymerization

Apparatus was set up as described previously [36]; a cylindrical glass tube (10 cm in diameter and 50 cm in length), enclosed by a pair of earthed metal flanges and encircled by a coil of copper wire, was evacuated to a base pressure of 1×10-3 mbar using a rotary pump and liquid N2 (nitrogen) cold trap. Microtitre plates, as well as a section of aluminium foil for X-ray photoelectron spectroscopy (XPS) analysis, were placed inside the 'in-coil' region of the reactor. Allylamine vapor was flowed through the reaction chamber at 4 cm3 stpmin-1 [38] giving a chamber pressure of 2×10-2 mbar. A 13.56 MHz radiofrequency at a continuous wave power of 5 W was used to excite the plasma within this chamber for a period of 15 min. XPS was carried out using a VG CLAM 2 XPS instrument, utilizing MgKα X-Rays and a take-off angle relative to the sample surface of 30 degrees. Quantification of polymerization was carried out using experimentally high derived sensitivity factors and linear background subtraction; samples were charge-corrected by setting the C1s peak position to 285.0 eV [39].

Microtitre Plate Assays

Binding assays, based on those described previously [30, 37], were carried out at room temperature to compare the binding of bA-Link_TSG6 (a biotinylated domain from human TSG-6 capable of binding Hp and HA) to untreated and allylamine plasma polymerized plates (MaxiSorp) following their incubation with HA or sources of Hp (see above). The plates were incubated with these glycosaminoglycans (GAGs) overnight at room temperature (at 0-10 µg/well) in 200 µl 20 mM Na2CO3 pH 9.6 or PBS. Plates were washed and blocked with 1% (v/v) BSA in pH 6.0-standard assay buffer (SAB-6; 50 mM Na-acetate, 100 mM NaCl, 0.2 % (v/v) Tween-20 pH 6.0) for 90 min at 37° C. as described before [30, 37]. The binding of bA-Link_TSG6 (2 pmol/well) was determined as reported previously [30]. Briefly, the wells were incubated with bA-Link_TSG6 in SAB-6 for 4 h at room temperature and then bound protein was detected by adding 200 µl/well of a 1:10,000 dilution of ExtrAvidin alkaline phosphatase (30 min) followed by 200 µl/well of 1 mg/ml disodium pnitrophenylphosphate in 0.05 M Tris-HCl, 0.1 M NaCl pH 9.3 and developed for 40 min. Absorbancies were read at 405 nm and corrected against blank wells. ELISAs were set up to detect the binding of Link_TSG6, KC or IL-8 to allylamine plates incubated overnight with 1.0 (Link_TSG6) or 0.5 (KC/IL-8) µg/well high molecular weight Hp in 200 µl PBS. Wells were washed in SAB-6 (Link_TSG6), or in the case of KC/IL-8 with SAB-7.2 (i.e., 50 mM Na-HEPES, 100 mM NaCl, 0.2% (v/v) Tween-20 pH 7.2), and blocked as described above. Wells were rewashed and incubated at room temperature with 0-50 pmol protein/well in 200 µl of the appropriate SAB. The interaction with Link_TSG6 was assessed by the addition of 1.25 µg Q75.2.10 mAb/well (in 200 µl SAB-6) for 45 min, followed by 200 µl/well of alkaline phosphatase-conjugated goat anti-rat IgG (1:2000) for an additional 45 min. The interactions with KC and IL-8 were determined by the addition of 0.03 µg/well of biotinylated anti-KC or anti-IL-8 antibodies in 100 µl SAB-7.2 for 90 min, followed by 0.02 µg/well ExtrAvidin-alkaline phosphatase in 200 µl SAB-7.2. ELISAs were developed by adding 200 µl/well of 1 mg/ml disodium p-nitrophenylphosphate in 0.05 M Tris-HCl, 0.1 M NaCl pH 9.3. Absorbancies were read at 405 nm after 5, 20 or 30 min for the TSG-6, IL-8 and KC assays, respectively, and corrected against blank wells.

In order to investigate the effect of salt on Hp immobilization, allylamine plates were coated with either high molecular weight Hp or the dp10 oligomer at 1 µg/well in PBS as described above. Plates were then incubated with SAB-6 containing 100-2000 mM NaCl for 1 h at room temperature. The plates were then washed once with SAB-6, before incubation with Link_TSG6 at 8 pmol/well for 4 h at room temperature under standard conditions. Bound protein was detected with the Q75.2.10 antibody as described above.

The utility of this assay for measuring heparin-protein interactions at a range of salt strengths was tested as follows. Heparin was coated onto allylamine plates at 1 µg/well (micrograms) and blocked as above. Factor H (FH) was then incubated with the plates (0-2.6 pmol/well) in SAB-7.2 containing 100, 250 or 400 mM NaCl for 4 h. Bound FH was detected with 1.25 µg/well OX23 mAb followed by alkaline phosphataseconjugated goat anti-mouse IgG (Sigma) diluted 1 in 1000 in SAB-7.2 (both incubated for 45 min) and developed for 5 min as described above.

EXAMPLE 1

XPS-analysis of the aluminium foil used in allylamine polymerization showed the presence of carbon, nitrogen and oxygen, but no aluminium (data not shown), indicating that polymerization depth is substantially thicker than the 8 nm XPS analysis depth. The presence of oxygen is due both to water vapor and residual air within the vacuum chamber during deposition, and to reactive groups within the plasma polymer film reacting with atmospheric oxygen and water vapor once the sample is exposed to air. FIG. 1 shows a typical XPS survey scan of an allylamine plasma polymer film. These films have an average N/C ratio of 0.24±0.01 (n=11) and an O/C ratio of 0.05±0.01 (n=11). Analysis of the C1s region (data not shown), and the presence of oxygen in the survey spectrum, indicated that the film contains not only amines retained from the monomer structure, but also a mixture of imines and amides at lower concentration. Further analysis of the C1s regions of nitrogen containing plasma polymer films is difficult to interpret due to the large overlap in chemical shifts between different finctional groups [39].

EXAMPLE 2

The results of plate assays presented in FIG. 2 show a clear difference in the ability of HA and Hp to bind to untreated and allylarnine plasma polymerized microtitre surfaces; this is based on their detection with the Link module from human TSG-6 (bA-Link_TSG6), a protein domain that can interact specifically with both of these GAGs (see [41]). When Hp was incubated for 18 h in PBS on allylamine plates, material remained bound to the well, and this was clearly in a functional form since it interacted with Link_TSG6 (FIG. 2a). However, no binding of Hp was observed when it was 'coated' onto untreated plates. Similarly if Hp was incubated with the allylamine-modified surfaces in Na2CO3, pH 9.6, rather than PBS, no binding of bA-10 Link_TSG6 was observed. From FIG. 2b it can be seen that, in contrast, functional HA (as determined by bA-Link_TSG6 binding) was immobilized on untreated plates when coated in Na2CO3 buffer; we have used assays of this type to characterize the interaction of TSG-6 with HA (see [30, 42, 43]). There was no binding detected when HA was incubated in PBS with untreated Maxisorb plates (although HA was seen to bind Nunc Polysorb plates under these conditions; data not shown), or when the allylamine-treated plates were 'coated' with HA in either buffer condition. The reason for these differences in coating is at present unclear, but may relate to different charge states of both GAG and surface at pH 7.4 and at pH 9.6. These results reveal that plasma polymerization with allylamine leads to a change in the surface of microtitre plates allowing the adherence of Hp.

EXAMPLE 3

FIG. 3 demonstrates that in addition to high molecular weight Hp (used in the above assays), low molecular weight preparations or even a Hp decasaccharide (i.e., dp10) can also be immobilized on these surfaces in functionally active states. Such defined oligosaccharides are particularly useful tools in the analysis of protein-GAG interactions and, therefore, assays of this type could be of great utility in the identification and characterization of Hp/HS-binding proteins.

EXAMPLE 4

The experiments described above were all performed using a biotinylated Hp-binding domain from TSG-6 to detect the presence of surface bound GAGs. FIG. 4 shows that the binding of this Link module and two chemokine proteins (i.e., murine KC and the well characterized Hp-binding protein human IL-8 [12]) to Hp coated plasma polymerized plates, could also be observed using antibody-based detection systems. As can be seen from FIG. 4, all of the proteins exhibit similar does response curves, although it should be noted that in the case of IL-8/KC, the assays take considerably longer to develop compared to Link_TSG6 (i.e., 20/30 min vs. 5 min, respectively); this may be due in part to the lower concentration of heparin used in the IL-8/KC assays, but may also indicate that these chemokines bind Hp less well than the TSG-6 Link module. Given that the allylamine surface is positively charged (at the pH values used here) it seemed likely that the interaction with Hp is ionic in nature. To test this hypothesis Hp (either high molecular weight or the dp10 oligomer) was coated onto allylamine plates as before, and these were then incubated with a range of salt strengths to determine what concentration of NaCl could displace Hp from the surface. Plates were then washed into SAB-6 and bound Hp detected with Link_TSG6 under standard conditions (i.e., 50 mM Na-acetate, 100 mM NaCl).

EXAMPLE 5

From FIG. 5 it is apparent that the binding of Hp to the allylamine surface is salt-strength dependent, which is consistent with this being an ionic interaction; e.g., 1 M NaCl reduced the amount of the immobilized high molecular weight Hp and 10-mer by 83% and 92%, respectively. In the case of the high molecular weight preparation, preincubation of the plates with 100-300 mM NaCl did not cause any reduction in the amount of bound Hp, and at 500 mM NaCl there was still 80% binding. As might be expected, the interaction of dp10 (~3 kDa) with the allylamine surface was somewhat more sensitive to salt than the high molecular weight Hp (~14 kDa); e.g., there was 87% and 64% binding of the 10-mer at 300 mM and 500 mM NaCl, respectively.

These data suggest that this assay system can be used across a wide range of salt strengths (e.g., 100-500 mM NaCl OR 0-100, 0-500, 500-750 mM NaCl).

EXAMPLE 6

To test this further we examined the binding of human complement factor H (a protein that has multiple Hp-binding sites [44]) to high molecular weight Hp at a range of NaCl concentrations. As can be seen from FIG. 6, similar levels of factor H binding to immobilized Hp were seen at 100 mM, 250 mM and 400 mM NaCl (corresponding to 150, 300 and 450 mM Na+ ions, respectively). Therefore, it would seem reasonable to conclude that microtitre plates plasma polymerized with allylamine can be used effectively to investigate a wide range Hp-protein interactions under various conditions of pH and salt strength using standard detection methodologies; for example, here we have examined the binding of four different proteins to heparin. In such cases covalent attachment of Hp to the plate surface would be preferable. Finally it should be noted that, since the plasma polymerization process is not limited to plastics, other surfaces can be coated with Hp in this manner. We believe that this could have significant utility in the development of reagents for glycomics research.

The invention claimed is:

1. A method for the selective disassociation of at least one bound glycosaminoglycan from a plasma polymerized surface of an organic monomer comprising an allylamine, said method comprising in consecutive order:
   providing a plasma polymerized surface comprising said allylamine;
   coating said plasma polymerized surface with a solution comprising phosphate buffered saline and at least one glycosaminoglycan;
   incubating said coated plasma polymerized surface to induce binding of said at least one glycosaminoglycan;
   contacting said surface with at least one agent having a salt concentration of about 500 mM NaCl to about 2 M NaCl, wherein said agent provides for selective disassociation of said at least one bound glycosaminoglycan from said plasma polymerized surface;
   washing said incubated coated plasma polymerized surface;
   incubating said washed plasma polymerized surface with a solution comprising tumor necrosis factor-inducible gene 6 protein (TSG-6); and
   detecting an amount of TSG-6 bound to said plasma polymerized surface, wherein said amount is inversely indicative of the selective disassociation of said at least one bound glycosaminoglycan from said plasma polymerized surface.

2. A method according to claim 1 wherein said glycosaminoglycan is a sulphated biomolecule.

3. A method according to claim 1 wherein said glycosaminoglycan is selected from the group consisting of: hyaluronan; dermatan sulfate; chondroitin sulphate; heparin; heparan sulphate; and keratan sulphate.

4. A method according to claim 1, wherein said agent has a salt concentration of about 500 mM NaCl to about 1 M NaCl.

5. A method according to claim 1, wherein said agent has a salt concentration of about 750 mM NaCl to about 1 M NaCl.

6. A method according to claim 1, wherein said agent has a salt concentration of about 500 mM NaCl to about 750 mM NaCl.

* * * * *